US009873884B2

(12) United States Patent
Unnikrishnan et al.

(10) Patent No.: US 9,873,884 B2
(45) Date of Patent: Jan. 23, 2018

(54) **MALE REPRODUCTIVE TISSUE AND STAGE SPECIFIC PROMOTERS FROM *EUCALYPTUS CAMALDULENSIS* SWEET GENE FAMILY MEMBER**

(71) Applicant: ITC LIMITED, Bangalore (IN)

(72) Inventors: Boby Vattekkattu Unnikrishnan, Bangalore (IN); Gurumurthy Demlapura Shankaranarayana, Bangalore (IN)

(73) Assignee: ITC Limited, Bangalore (IN)

( * ) Notice: Subject to any disclaimer, the term of this patent is extended or adjusted under 35 U.S.C. 154(b) by 0 days.

(21) Appl. No.: 15/030,328

(22) PCT Filed: Oct. 13, 2014

(86) PCT No.: PCT/IB2014/002074
§ 371 (c)(1),
(2) Date: Apr. 18, 2016

(87) PCT Pub. No.: WO2015/056070
PCT Pub. Date: Apr. 23, 2015

(65) Prior Publication Data
US 2016/0272983 A1    Sep. 22, 2016

(30) Foreign Application Priority Data

Oct. 18, 2013    (IN) ............................ 4719/CHE/2013

(51) Int. Cl.
*C12N 15/82*    (2006.01)
*C07K 14/415*    (2006.01)

(52) U.S. Cl.
CPC ........ *C12N 15/8231* (2013.01); *C07K 14/415* (2013.01); *C12N 15/827* (2013.01); *C12N 15/8241* (2013.01); *C12N 15/8265* (2013.01)

(58) Field of Classification Search
None
See application file for complete search history.

(56) References Cited

U.S. PATENT DOCUMENTS 6,563,024 B1 *    5/2003    Kawazu ............. C12N 15/8205
435/419

FOREIGN PATENT DOCUMENTS

WO    WO 2013/086494 A1    6/2013
WO    WO 2014/159845 A1    10/2014

OTHER PUBLICATIONS

Hirakawa et al. Survey of the genetic information carried in the genome of *Eucalyptus camaldulensis*. (2011) Plant Biotechnology; vol. 28; pp. 471-480.*
Donald et al. Mutation of either G box or I box sequences profoundly affects expression from the Arabidopsis rbcS-1A promoter. (1990) EMBO J.; vol. 9; pp. 1717-1726.*
Eyal et al. Pollen specificity elements reside in 30 bp of the proximal promoters of two pollen-expressed genes. (1995) Plant Cell; vol. 7; pp. 373-384.*
Chen et al. Minimal regions in the *Arabidopsis* PISTILLATA promoter responsive to the APETALA3/PISTILLATA feedback control do not contain a CArG box. (2000) Sex. Plant Reprod.; vol. 13; pp. 85-94.*
Benfey et al. The cauliflower mosaic virus 35S promoter: combinatorial regulation of transcription in plants. (1990) Science; vol. 250; pp. 959-966.*
Kim et al. A 20 nucleotide upstream element is essential for the noplaine synthase (nos) promoter activity. (1994) Plant Mol. Biol.; vol. 24; pp. 105-117.*
PCT International Search Report for PCT/IB2014/002074, dated Jan. 29, 2015, 5 pages.
PCT Written Opinion of the International Searching Authority for PCT/IB2014/002074, dated Jan. 29, 2015, 6 pages.
Thomas L. Slewinski: "Diverse Functional Roles of Monosaccharide Transporters and their Homologs in Vascular Plants: A Physiological Perspective". Molecular Plant, vol. 4, No. 4, Jul. 1, 2011 (Jul. 1, 2011), pp. 641-662, XP055161648, ISSN: 1674-2052, DOI: 10.1093/mp/ssr051.
Li-Qing Chen et al: "Sugar transporters for intercellular exchange and nutrition of pathogens", Nature, Nature Publishing Group, United Kingdom, vol. 468, No. 7323, Nov. 25, 2010, (Nov. 25, 2010), pp. 527-532, XP002682416, ISSN: 0028-0836, DOI: 10.1038/NATURE09606 [retrieved on Nov. 24, 2010].
DiFazion et al., "Gene flow form tree plantations and implications for transgenic risk assessment", Plantation Forest Biotechnology for the 21st Century, 2004, 405-422.
Zhang et al., "Breakthrough Technologies, Control of Pollen-Mediated Gene Flow in Transgenic Trees", Plant Physiol., 159(4), 1319-1334.
Slewinski, Thomas L., "Diverse Functional Roles of Monosaccharide Transporters and their Homologs in Vascular Plants : A Physiological Perspective", Molecular Plant (Jul. 2011) vol. 4, No. 4, doi:10.1093/mp/ssr051; pp. 641-662.

* cited by examiner

*Primary Examiner* — Cathy Kingdon Worley
(74) *Attorney, Agent, or Firm* — Brian L. Stender; Patterson Thuente Pedersen, P.A.

(57) ABSTRACT

The present application discloses polynucleotide fragment(s) encoding a male reproductive tissue-specific promoter obtained from a family member of the SWEET gene family of *Eucalyptus camaldulensis*, as well as a polynucleotide sequence comprising the promoter fragment and an operably-linked heterologous polynucleotide, and a method of using the polynucleotide sequence to express a heterologous polynucleotide exclusively in male reproductive tissues of a plant.

23 Claims, 5 Drawing Sheets

MALE REPRODUCTIVE TISSUE AND STAGE SPECIFIC PROMOTERS FROM *EUCALYPTUS CAMALDULENSIS* SWEET GENE FAMILY MEMBER

RELATED APPLICATIONS

The present application is a National Phase entry of PCT Application No. PCT/IB2014/002074, filed Oct. 13, 2014, which claims priority from IN Patent Application No. 4719/CHE/2013, filed Oct. 18, 2013, said applications being hereby incorporated by reference herein in their entireties.

FIELD OF INVENTION

The present disclosure relates to plant molecular biology and genetic engineering, in particular the isolation and characterization of a male reproductive organ specific promoter from *Eucalyptus camaldulensis*, particularly a DNA sequence capable of driving expression of an operably linked transcribable polynucleotide fragment.

BACKGROUND OF THE INVENTION

A major issue for plant genetic engineering is the extent to which transgenes can escape from cultivation and negatively impact the ecosystem. The pollen from transgenic plants may impart wild plants with better fitness or aid in transfer of genes of resistance especially during negative selections processes. This kind of gene flow is of particular concern in forest trees because trees are virtually undomesticated and are likely to be present within potential mating proximity of transgenic cultivated plants and trees, leading to contamination of the wild germplasm (DiFazio et al., *Plantation Forest Biotechnology for the 21st Century*, 2004, 405-422).

A reproductive tissue specific promoter offers a solution for containing the gene flow from transgenic trees into the wild. There are various mechanisms being developed to prevent gene flow from transgenic plants to related or wild germplasm. This includes the use of cytotoxic genes under the control of reproductive tissue specific promoters or the use of gene excision mechanisms at time of reproductive tissue development. Until now, very limited success has been achieved in controlling pollen production in trees. Recently, the PrMC2-barnaseH102E expression cassette was found to efficiently ablate pollen in tobacco, pine and *eucalyptus*. The field performance of the PrMC2-barnaseH102E in representative angiosperm and gymnosperm trees indicated that this cassette can be used to mitigate pollen-mediated gene flow concerns associated with large scale deployment of transgenic trees (Zhang et al. *Plant Physiol.*, 2012, 159(4), 1319-1334).

SUMMARY OF THE INVENTION

This summary is provided to introduce concepts related to plant molecular biology and genetic engineering, in particular the isolation and characterization of a male organ specific promoter from *Eucalyptus camaldulensis*. This summary is not intended to identify essential features of the claimed subject matter nor is it intended for use in determining or limiting the scope of the claimed subject matter.

An aspect of the present disclosure relates to a DNA sequence capable of driving expression of an operably linked transcribable polynucleotide fragment, said DNA sequence having polynucleotide sequence at least 85% similar to a sequence as set forth in SEQ ID NO: 1 or SEQ ID NO: 4 or SEQ ID NO: 7.

An aspect of the present disclosure relates to a recombinant DNA construct comprising of a DNA sequence capable of driving expression of an operably linked transcribable polynucleotide fragment, said DNA sequence having polynucleotide sequence at least 85% similar to a sequence as set forth in SEQ ID NO: 1 or SEQ ID NO: 4 or SEQ ID NO: 7.

Another aspect of the present disclosure relates to a recombinant vector comprising a recombinant DNA construct comprising of a DNA sequence capable of driving expression of an operably linked transcribable polynucleotide fragment, said DNA sequence having polynucleotide sequence at least 85% similar to a sequence as set forth in SEQ ID NO: 1 or SEQ ID NO: 4 or SEQ ID NO: 7.

Still another aspect of the present disclosure provides a recombinant host cell comprising a DNA sequence capable of driving expression of an operably linked transcribable polynucleotide fragment, said DNA sequence having polynucleotide sequence at least 85% similar to a sequence as set forth in SEQ ID NO: 1 or SEQ ID NO: 4 or SEQ ID NO: 7.

Yet another aspect of the present disclosure relates to a transgenic plant or parts thereof including seeds, wherein said transgenic plant or parts thereof including seeds comprise of a DNA sequence having polynucleotide sequence at least 85% similar to a sequence as set forth in SEQ ID NO: 1 or SEQ ID NO: 4 or SEQ ID NO: 7.

An aspect of the present disclosure relates to use of a DNA sequence having polynucleotide sequence at least 85% similar to a sequence as set forth in SEQ ID NO: 1 or SEQ ID NO: 4 or SEQ ID NO: 7 to drive expression of an operably linked transcribable polynucleotide fragment in a plant.

Another aspect of the present disclosure provides a method of generating a transgenic plant comprising of a DNA sequence having polynucleotide sequence at least 85% similar to a sequence as set forth in SEQ ID NO: 1 or SEQ ID NO: 4 or SEQ ID NO: 7, wherein the said method comprises: (a) obtaining a recombinant host cell comprising a DNA sequence capable of driving expression of an operably linked transcribable polynucleotide fragment, said DNA sequence having polynucleotide sequence at least 85% similar to a sequence as set forth in SEQ ID NO: 1 or SEQ ID NO: 4 or SEQ ID NO: 7; (b) obtaining a plant cell; (c) transforming said plant cell with said recombinant host cell; (d) selecting a transformed plant cell comprising of said DNA sequence; and (e) developing a transgenic plant from said transformed plant cell.

These and other features, aspects and advantages of the present subject matter will be better understood with reference to the following description and appended claims. This summary is provided to introduce a selection of concepts. This summary is not intended to identify key features or essential features of the claimed subject matter, nor is it intended to be used for to limiting the scope of the claimed subject matter.

BRIEF DESCRIPTION OF THE ACCOMPANYING DRAWINGS

The following drawings form part of the present specification and are included to further illustrate aspects of the present invention. The invention may be better understood

DETAILED DESCRIPTION OF THE INVENTION

Those skilled in the art will be aware that the invention described herein is subject to variations and modifications other than those specifically described. It is to be understood that the invention described herein includes all such variations and modifications. The invention also includes all such steps, features, compositions and compounds referred to or indicated in this specification, individually or collectively, and any and all combinations of any or more of such steps or features.

Definitions

For convenience, before further description of the present invention, certain terms employed in the specification, example and appended claims are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The term "plurality" means more than one.

The terms "at least two", "more than one" and "plurality" are used interchangeably.

The terms "comprise" and "comprising" are used in the inclusive, open sense, meaning that additional elements may be included. It is not intended to be construed as "consists of only.

Throughout this specification, unless the context requires otherwise the word "comprise", and variations such as "comprises" and "comprising", will be understood to imply the inclusion of a stated element or step or group of element or steps but not the exclusion of any other element or step or group of element or steps. The term "including" is used to mean "including but not limited to". "Including" and "including but not limited to" are used interchangeably.

The term "Heterologous Gene/DNA" refers to DNA sequence of foreign origin inserted into the plant genome.

The term "polynucleotide" or "polynucleotide molecule" or "polynucleotide sequence" used herein refers to the single or double stranded DNA or RNA of genomic or synthetic origin, i.e., a polymer of deoxyribonucleotide or ribonucleotide bases, respectively, read from the 5' (upstream) end to the 3' (downstream) end.

The term "nucleotide sequence" as used herein refers to the sequence of a polynucleotide molecule.

The term "promoter" as used herein, refers to a polynucleotide molecule that is in its native or non native state located upstream or 5' to a translational start codon of an open reading frame (or protein-coding region) and that is involved in recognition and binding of RNA polymerase II and other proteins (trans-acting transcription factors) to initiate transcription.

A "plant promoter" is a native or non-native promoter that is functional in plant cells. Constitutive plant promoters are functional in most or all tissues of a plant throughout plant development. Any plant promoter can be used as a 5' regulatory element for modulating expression of a particular gene or genes operably associated thereto. When operably linked to a polynucleotide molecule, a promoter typically causes the polynucleotide molecule to be transcribed in a manner that is similar to that of which the promoter is normally associated.

Polynucleotide molecules that are capable of regulating transcription of operably linked genes and are substantially homologous to the polynucleotide sequences of the promoter provided herein are encompassed within the scope of this invention.

Optimal alignment of polynucleotide or polypeptide sequences are well known to those skilled in the art and may be conducted by tools such as BLAST, CLUSTAL W, CLUSTAL X, T-COFFEE etc.

The term "homology" as used herein, refers to the level of similarity or percent identity between polynucleotide sequences in terms of percent nucleotide positional identity, i.e., sequence similarity or identity. The term homology also refers to the concept of similar functional properties among different polynucleotide molecules, e.g., promoters that have similar function may have homologous cis-elements.

Polynucleotide molecules are homologous when under certain conditions they specifically hybridize to form a duplex molecule. Under these conditions, referred to as stringency conditions, one polynucleotide molecule can be used as a probe or primer to identify other polynucleotide molecules that share homology.

The terms "Recombinant DNA expression construct" and "recombinant DNA molecule" used herein can be used interchangeably.

As used herein the term "marker gene" refers to any polynucleotide molecule expression of which can be screened for or scored in some manner.

As used herein, the term "gene of agronomic interest" refers to a polynucleotide molecule that includes but is not limited to a gene that provides a desirable characteristic associated with plant morphology, physiology, growth and development, yield, nutritional enhancement, disease or pest resistance, or environmental, physical strength or chemical tolerance.

In particular, the present disclosure relates to the isolation and characterization of a male reproductive organ specific promoter from *Eucalyptus camaldulensis*, wherein the promoter is capable of driving expressing one or more target genes in a plant.

In an embodiment of the present disclosure, there is provided a DNA sequence capable of driving expression of an operably linked transcribable polynucleotide fragment, said DNA sequence having polynucleotide sequence at least 85% similar to a sequence as set forth in SEQ ID NO: 1 or SEQ ID NO: 4 or SEQ ID NO: 7.

In an embodiment of the present disclosure, there is provided a DNA sequence as described herein, said DNA sequence having polynucleotide sequence at least 85%, 86%, 87%, 88%, 89%, 90%, 91%, 92%, 93%, 94%, 95%, 96%, 97%, 98%, or 99% similar to a sequence as set forth in SEQ ID NO: 1 or SEQ ID NO: 4 or SEQ ID NO: 7.

In a preferred embodiment of the present disclosure, there is provided a DNA sequence as described herein, said DNA sequence having polynucleotide sequence 100% similar to a sequence as set forth in SEQ ID NO: 1 or SEQ ID NO: 4 or SEQ ID NO: 7

In an embodiment of the present disclosure, there is provided a DNA sequence as described herein, said DNA sequence having polynucleotide sequence at least 85% similar to a sequence as set forth in SEQ ID NO: 1.

In an embodiment of the present disclosure, there is provided a DNA sequence as described herein, said DNA sequence having polynucleotide sequence at least 85%, 86%, 87%, 88%, 89%, 90%, 91%, 92%, 93%, 94%, 95%, 96%, 97%, 98%, or 99% similar to a sequence as set forth in SEQ ID NO: 1.

In a preferred embodiment of the present disclosure, there is provided a DNA sequence as described herein, said DNA sequence having polynucleotide sequence 100% similar to a sequence as set forth in SEQ ID NO: 1.

In an embodiment of the present disclosure, there is provided a DNA sequence as described herein, said DNA sequence having polynucleotide sequence at least 85% similar to a sequence as set forth in SEQ ID NO: 4.

In an embodiment of the present disclosure, there is provided a DNA sequence as described herein, said DNA sequence having polynucleotide sequence at least 85%, 86%, 87%, 88%, 89%, 90%, 91%, 92%, 93%, 94%, 95%, 96%, 97%, 98%, or 99% similar to a sequence as set forth in SEQ ID NO: 4.

In a preferred embodiment of the present disclosure, there is provided a DNA sequence as described herein, said DNA sequence having polynucleotide sequence 100% similar to a sequence as set forth in SEQ ID NO: 4.

In an embodiment of the present disclosure, there is provided a DNA sequence as described herein, said DNA sequence having a polynucleotide sequence at least 85% similar to a sequence as set forth in SEQ ID NO: 7.

In an embodiment of the present disclosure, there is provided a DNA sequence as described herein, said DNA sequence having polynucleotide sequence at least 85%, 86%, 87%, 88%, 89%, 90%, 91%, 92%, 93%, 94%, 95%, 96%, 97%, 98%, or 99% similar to a sequence as set forth in SEQ ID NO: 7.

In a preferred embodiment of the present disclosure, there is provided a DNA sequence as described herein, said DNA sequence having polynucleotide sequence 100% similar to a sequence as set forth in SEQ ID NO: 7.

In an embodiment of the present disclosure, there is provided a DNA sequence as described herein, said DNA sequence having polynucleotide sequence as set forth in SEQ ID NO: 1, consisting of at least 247 contiguous nucleotides as set forth in SEQ ID NO: 7.

In an embodiment of the present disclosure, there is provided a DNA sequence as described herein, said DNA sequence drives expression of an operably linked transcribable polynucleotide fragment in a tissue specific manner.

In a preferred embodiment of the present disclosure, there is provided a DNA sequence that drives expression of an operably linked transcribable polynucleotide fragment in a tissue specific manner as described herein, wherein said tissue is plant reproductive organ.

In a more preferred embodiment of the present disclosure, there is provided a DNA sequence that drives expression of an operably linked transcribable polynucleotide fragment in a tissue specific manner as described herein, wherein said tissue is plant male reproductive organ.

In an embodiment of the present disclosure, there is provided a DNA sequence that drives expression of an operably linked transcribable polynucleotide fragment in a tissue specific manner as described herein, wherein said DNA sequence drives expression in a tissue stage specific manner.

In an embodiment of the present disclosure, there is provided a recombinant DNA construct comprising of a DNA sequence as described herein.

In an embodiment of the present disclosure, there is provided a recombinant DNA construct comprising of a DNA sequence capable of driving expression of an operably linked transcribable polynucleotide fragment, said DNA sequence having polynucleotide sequence at least 85%, 86%, 87%, 88%, 89%, 90%, 91%, 92%, 93%, 94%, 95%, 96%, 97%, 98%, or 99% similar to a sequence as set forth in SEQ ID NO: 1.

In an embodiment of the present disclosure, there is provided a recombinant DNA construct comprising of a DNA sequence capable of driving expression of an operably linked transcribable polynucleotide fragment, said DNA sequence having polynucleotide sequence as set forth in SEQ ID NO: 1.

In an embodiment of the present disclosure, there is provided a recombinant DNA construct comprising of a DNA sequence capable of driving expression of an operably linked transcribable polynucleotide fragment, said DNA sequence having polynucleotide sequence at least 85%, 86%, 87%, 88%, 89%, 90%, 91%, 92%, 93%, 94%, 95%, 96%, 97%, 98%, or 99% similar to a sequence as set forth in SEQ ID NO: 4.

In an embodiment of the present disclosure, there is provided a recombinant DNA construct comprising of a DNA sequence capable of driving expression of an operably linked transcribable polynucleotide fragment, said DNA sequence having polynucleotide sequence as set forth in SEQ ID NO: 4.

In an embodiment of the present disclosure, there is provided a recombinant DNA construct comprising of a DNA sequence capable of driving expression of an operably linked transcribable polynucleotide fragment, said DNA sequence having polynucleotide sequence at least 85%, 86%, 87%, 88%, 89%, 90%, 91%, 92%, 93%, 94%, 95%, 96%, 97%, 98%, or 99% similar to a sequence as set forth in SEQ ID NO: 7.

In an embodiment of the present disclosure, there is provided a recombinant DNA construct comprising of a DNA sequence capable of driving expression of an operably linked transcribable polynucleotide fragment, said DNA sequence having polynucleotide sequence as set forth in SEQ ID NO: 7.

In an embodiment of the present disclosure, there is provided a recombinant DNA vector comprising of a DNA sequence as described herein.

In an embodiment of the present disclosure, there is provided a recombinant DNA vector comprising of a DNA sequence capable of driving expression of an operably linked transcribable polynucleotide fragment, said DNA sequence having polynucleotide sequence at least 85%, 86%, 87%, 88%, 89%, 90%, 91%, 92%, 93%, 94%, 95%, 96%, 97%, 98%, or 99% similar to a sequence as set forth in SEQ ID NO: 1.

In an embodiment of the present disclosure, there is provided a recombinant DNA vector comprising of a DNA sequence capable of driving expression of an operably linked transcribable polynucleotide fragment, said DNA sequence having polynucleotide sequence as set forth in SEQ ID NO: 1.

In an embodiment of the present disclosure, there is provided a recombinant DNA vector comprising of a DNA sequence capable of driving expression of an operably linked transcribable polynucleotide fragment, said DNA sequence having polynucleotide sequence at least 85%, 86%, 87%, 88%, 89%, 90%, 91%, 92%, 93%, 94%, 95%, 96%, 97%, 98%, or 99% similar to a sequence as set forth in SEQ ID NO: 4.

In an embodiment of the present disclosure, there is provided a recombinant DNA vector comprising of a DNA sequence capable of driving expression of an operably linked transcribable polynucleotide fragment, said DNA sequence having polynucleotide sequence as set forth in SEQ ID NO: 4.

In an embodiment of the present disclosure, there is provided a recombinant DNA vector comprising of a DNA sequence capable of driving expression of an operably linked transcribable polynucleotide fragment, said DNA sequence having polynucleotide sequence at least 85%, 86%, 87%, 88%, 89%, 90%, 91%, 92%, 93%, 94%, 95%, 96%, 97%, 98%, or 99% similar to a sequence as set forth in SEQ ID NO: 7.

In an embodiment of the present disclosure, there is provided a recombinant DNA vector comprising of a DNA sequence capable of driving expression of an operably linked transcribable polynucleotide fragment, said DNA sequence having polynucleotide sequence as set forth in SEQ ID NO: 7.

In an embodiment of the present disclosure, there is provided a recombinant DNA vector comprising a recombinant DNA construct as described herein.

In an embodiment of the present disclosure, there is provided a recombinant host cell comprising of a DNA sequence as described herein.

In an embodiment of the present disclosure, there is provided a recombinant host cell comprising of a DNA sequence capable of driving expression of an operably linked transcribable polynucleotide fragment, said DNA sequence having polynucleotide sequence at least 85%, 86%, 87%, 88%, 89%, 90%, 91%, 92%, 93%, 94%, 95%, 96%, 97%, 98%, or 99% similar to a sequence as set forth in SEQ ID NO: 1.

In an embodiment of the present disclosure, there is provided a recombinant host cell comprising of a DNA sequence capable of driving expression of an operably linked transcribable polynucleotide fragment, said DNA sequence having polynucleotide sequence as set forth in SEQ ID NO: 1.

In an embodiment of the present disclosure, there is provided a recombinant host cell comprising of a DNA sequence capable of driving expression of an operably linked transcribable polynucleotide fragment, said DNA sequence having polynucleotide sequence at least 85%, 86%, 87%, 88%, 89%, 90%, 91%, 92%, 93%, 94%, 95%, 96%, 97%, 98%, or 99% similar to a sequence as set forth in SEQ ID NO: 4.

In an embodiment of the present disclosure, there is provided a recombinant host cell comprising of a DNA sequence capable of driving expression of an operably linked transcribable polynucleotide fragment, said DNA sequence having polynucleotide sequence as set forth in SEQ ID NO: 4.

In an embodiment of the present disclosure, there is provided a recombinant host cell comprising of a DNA sequence capable of driving expression of an operably linked transcribable polynucleotide fragment, said DNA sequence having polynucleotide sequence at least 85%, 86%, 87%, 88%, 89%, 90%, 91%, 92%, 93%, 94%, 95%, 96%, 97%, 98%, or 99% similar to a sequence as set forth in SEQ ID NO: 7.

In an embodiment of the present disclosure, there is provided a recombinant host cell comprising of a DNA sequence capable of driving expression of an operably linked transcribable polynucleotide fragment, said DNA sequence having polynucleotide sequence as set forth in SEQ ID NO: 7.

In an embodiment of the present disclosure, expression of said transcribable polynucleotide fragment operably linked to a DNA sequence as described herein confers male sterility.

In an embodiment of the present disclosure, expression of said transcribable polynucleotide fragment operably linked to a DNA sequence as described herein confers insecticide resistance.

In an embodiment of the present disclosure, expression of said transcribable polynucleotide fragment operably linked to a DNA sequence as described herein confers herbicide resistance.

In an embodiment of the present disclosure, expression of said transcribable polynucleotide fragment operably linked to a DNA sequence as described herein confers abiotic stress resistance.

In an embodiment of the present disclosure, expression of said transcribable polynucleotide fragment operably linked to a DNA sequence as described herein results in pollen ablation.

In an embodiment of the present disclosure, expression of said transcribable polynucleotide fragment operably linked to a DNA sequence as described herein results in activation of gene excision mechanisms.

In an embodiment of the present disclosure, there is provided a recombinant host cell as described herein, wherein said recombinant host cell is a bacterial or a fungal or a plant cell.

In an embodiment of the present disclosure, there is provided a recombinant host cell as described herein, wherein said recombinant host cell is a bacterial cell.

In an embodiment of the present disclosure, there is provided a recombinant host cell as described herein, wherein said recombinant host cell is *Agrobacterium tumefaciens*.

In an embodiment of the present disclosure, there is provided a recombinant host cell as described herein, wherein said recombinant host cell is a fungal cell.

In an embodiment of the present disclosure, there is provided a recombinant host cell as described herein, wherein said recombinant host cell is a plant cell.

In an embodiment of the present disclosure, there is provided a recombinant host cell as described herein, wherein said recombinant host cell is a plant cell selected from the group of plants consisting of wheat, rice, barley, oats, potato, soybean, tobacco, *eucalyptus*, subabul, *casuarina*, corymbia, poplar, and acacia.

In an embodiment of the present disclosure, there is provided a recombinant DNA construct as described herein, further comprising of a transcription terminator.

In an embodiment of the present disclosure, there is provided a transgenic plant or parts thereof including seeds comprising of a DNA sequence capable of driving expression of an operably linked transcribable polynucleotide fragment, said DNA sequence having polynucleotide sequence at least 85% similar to a sequence as set forth in SEQ ID NO: 1 or SEQ ID NO: 4 or SEQ ID NO: 7.

In an embodiment of the present disclosure, there is provided a transgenic plant or parts thereof including seeds comprising of DNA sequence capable of driving expression of an operably linked transcribable polynucleotide fragment, said DNA sequence having polynucleotide sequence at least 85%, 86%, 87%, 88%, 89%, 90%, 91%, 92%, 93%, 94%, 95%, 96%, 97%, 98%, or 99% similar to a sequence as set forth in SEQ ID NO: 1.

In an embodiment of the present disclosure, there is provided a transgenic plant or parts thereof including seeds comprising of DNA sequence capable of driving expression of an operably linked transcribable polynucleotide fragment, said DNA sequence having polynucleotide sequence as set forth in SEQ ID NO: 1.

In an embodiment of the present disclosure, there is provided a transgenic plant or parts thereof including seeds comprising of DNA sequence capable of driving expression of an operably linked transcribable polynucleotide fragment, said DNA sequence having polynucleotide sequence at least 85%, 86%, 87%, 88%, 89%, 90%, 91%, 92%, 93%, 94%, 95%, 96%, 97%, 98%, or 99% similar to a sequence as set forth in SEQ ID NO: 4.

In an embodiment of the present disclosure, there is provided a transgenic plant or parts thereof including seeds comprising of DNA sequence capable of driving expression of an operably linked transcribable polynucleotide fragment, said DNA sequence having polynucleotide sequence as set forth in SEQ ID NO: 4.

In an embodiment of the present disclosure, there is provided a transgenic plant or parts thereof including seeds comprising of DNA sequence capable of driving expression of an operably linked transcribable polynucleotide fragment, said DNA sequence having polynucleotide sequence at least 85%, 86%, 87%, 88%, 89%, 90%, 91%, 92%, 93%, 94%, 95%, 96%, 97%, 98%, or 99% similar to a sequence as set forth in SEQ ID NO: 7.

In an embodiment of the present disclosure, there is provided a transgenic plant or parts thereof including seeds comprising of DNA sequence capable of driving expression of an operably linked transcribable polynucleotide fragment, said DNA sequence having polynucleotide sequence as set forth in SEQ ID NO: 7.

In an embodiment of the present disclosure, there is provided a transgenic plant or parts thereof including seeds, wherein said transgenic plant or parts thereof including seeds in a monocot or a dicot.

In an embodiment of the present disclosure, there is provided a transgenic plant or parts thereof including seeds, wherein said transgenic plant or parts thereof including seeds in a monocot.

In an embodiment of the present disclosure, there is provided a transgenic plant or parts thereof including seeds, wherein said transgenic plant or parts thereof including seeds in a dicot.

In an embodiment of the present disclosure, there is provided a transgenic plant or parts thereof including seeds, wherein said transgenic plant or parts thereof including seeds is selected from the group consisting of wheat, rice, barley, oats, potato, soybean, tobacco, *eucalyptus*, subabul, *casuarina*, corymbia, poplar, and acacia.

In an embodiment of the present disclosure, there is provided a use of a DNA sequence as described herein to drive expression of an operably linked transcribable polynucleotide fragment in a plant.

In an embodiment of the present disclosure, there is provided a use of a DNA sequence to drive expression of an operably linked transcribable polynucleotide fragment in a plant as described herein, wherein said DNA sequence has polynucleotide fragment at least 85%, 86%, 87%, 88%, 89%, 90%, 91%, 92%, 93%, 94%, 95%, 96%, 97%, 98%, or 99% similar to a sequence as set forth in SEQ ID NO: 1.

In an embodiment of the present disclosure, there is provided a use of a DNA sequence to drive expression of an operably linked transcribable polynucleotide fragment in a plant as described herein, wherein said DNA sequence has polynucleotide fragment as set forth in SEQ ID NO: 1.

In an embodiment of the present disclosure, there is provided a use of a DNA sequence to drive expression of an operably linked transcribable polynucleotide fragment in a plant as described herein, wherein said DNA sequence has polynucleotide fragment at least 85%, 86%, 87%, 88%, 89%, 90%, 91%, 92%, 93%, 94%, 95%, 96%, 97%, 98%, or 99% similar to a sequence as set forth in SEQ ID NO: 4.

In an embodiment of the present disclosure, there is provided a use of a DNA sequence to drive expression of an operably linked transcribable polynucleotide fragment in a plant as described herein, wherein said DNA sequence has polynucleotide fragment as set forth in SEQ ID NO: 4.

In an embodiment of the present disclosure, there is provided a use of a DNA sequence to drive expression of an operably linked transcribable polynucleotide fragment in a plant as described herein, wherein said DNA sequence has polynucleotide fragment at least 85%, 86%, 87%, 88%, 89%, 90%, 91%, 92%, 93%, 94%, 95%, 96%, 97%, 98%, or 99% similar to a sequence as set forth in SEQ ID NO: 7.

In an embodiment of the present disclosure, there is provided a use of a DNA sequence to drive expression of an operably linked transcribable polynucleotide fragment in a plant as described herein, wherein said DNA sequence has polynucleotide fragment as set forth in SEQ ID NO: 7.

In an embodiment of the present disclosure, there is provided a method of generating a transgenic plant comprising of a DNA sequence capable of driving expression of an operably linked transcribable polynucleotide fragment, said DNA sequence having polynucleotide sequence at least 85% similar to a sequence as set forth in SEQ ID NO: 1 or SEQ ID NO: 4 or SEQ ID NO: 7, said method comprising of (a) obtaining a recombinant host cell comprising of a DNA sequence capable of driving expression of an operably linked transcribable polynucleotide fragment, said DNA sequence having polynucleotide sequence at least 85% similar to a sequence as set forth in SEQ ID NO: 1 or SEQ ID NO: 4 or SEQ ID NO: 7; (b) obtaining a plant cell; (c) transforming said plant cell with said recombinant host cell; (d) selecting a transformed plant cell comprising of said DNA sequence; and (e) developing a transgenic plant from said transformed plant cell.

In an embodiment of the present disclosure, there is provided a method of generating a transgenic plant as described herein, wherein said plant cell is a monocot or a dicot.

In an embodiment of the present disclosure, there is provided a method of generating a transgenic plant as described herein, wherein said plant cell is a monocot.

In an embodiment of the present disclosure, there is provided a method of generating a transgenic plant as described herein, wherein said plant cell is a dicot.

In an embodiment of the present disclosure, there is provided a method of generating a transgenic plant as described herein, wherein said plant is selected from the group consisting of wheat, rice, barley, oats, potato, soybean, tobacco, *eucalyptus*, subabul, *casuarina*, corymbia, poplar, and acacia.

In a preferred embodiment of the present disclosure, there is provided a method of generating a transgenic plant as described herein, wherein said plant is tobacco.

In a preferred embodiment of the present disclosure, there is provided a method of generating a transgenic plant as described herein, wherein said plant is *eucalyptus*.

In an embodiment of the present disclosure, there is provided a method of generating a transgenic plant comprising of a DNA sequence capable of driving expression of an operably linked transcribable polynucleotide fragment, said DNA sequence having polynucleotide sequence at least 85%, 86%, 87%, 88%, 89%, 90%, 91%, 92%, 93%, 94%, 95%, 96%, 97%, 98%, or 99% similar to a sequence as set forth in SEQ ID NO: 1; (b) obtaining a plant cell; (c) transforming said plant cell with said recombinant host cell; (d) selecting a transformed plant cell comprising of said DNA sequence; and (e) developing a transgenic plant from said transformed plant cell.

In an embodiment of the present disclosure, there is provided a method of generating a transgenic plant comprising of a DNA sequence capable of driving expression of an operably linked transcribable polynucleotide fragment, said DNA sequence having polynucleotide sequence as set forth in SEQ ID NO: 1; (b) obtaining a plant cell; (c) transforming said plant cell with said recombinant host cell; (d) selecting a transformed plant cell comprising of said DNA sequence; and (e) developing a transgenic plant from said transformed plant cell In an embodiment of the present disclosure, there is provided a method of generating a transgenic plant comprising of a DNA sequence capable of driving expression of an operably linked transcribable polynucleotide fragment, said DNA sequence having polynucleotide sequence at least 85%, 86%, 87%, 88%, 89%, 90%, 91%, 92%, 93%, 94%, 95%, 96%, 97%, 98%, or 99% similar to a sequence as set forth in SEQ ID NO: 4; (b) obtaining a plant cell; (c) transforming said plant cell with said recombinant host cell; (d) selecting a transformed plant cell comprising of said DNA sequence; and (e) developing a transgenic plant from said transformed plant cell.

In an embodiment of the present disclosure, there is provided a method of generating a transgenic plant comprising of a DNA sequence capable of driving expression of an operably linked transcribable polynucleotide fragment, said DNA sequence having polynucleotide sequence as set forth in SEQ ID NO: 4; (b) obtaining a plant cell; (c) transforming said plant cell with said recombinant host cell; (d) selecting a transformed plant cell comprising of said DNA sequence; and (e) developing a transgenic plant from said transformed plant cell In an embodiment of the present disclosure, there is provided a method of generating a transgenic plant comprising of a DNA sequence capable of driving expression of an operably linked transcribable polynucleotide fragment, said DNA sequence having polynucleotide sequence at least 85%, 86%, 87%, 88%, 89%, 90%, 91%, 92%, 93%, 94%, 95%, 96%, 97%, 98%, or 99% similar to a sequence as set forth in SEQ ID NO: 7; (b) obtaining a plant cell; (c) transforming said plant cell with said recombinant host cell; (d) selecting a transformed plant cell comprising of said DNA sequence; and (e) developing a transgenic plant from said transformed plant cell.

In an embodiment of the present disclosure, there is provided a method of generating a transgenic plant comprising of a DNA sequence capable of driving expression of an operably linked transcribable polynucleotide fragment, said DNA sequence having polynucleotide sequence as set forth in SEQ ID NO: 7; (b) obtaining a plant cell; (c) transforming said plant cell with said recombinant host cell; (d) selecting a transformed plant cell comprising of said DNA sequence; and (e) developing a transgenic plant from said transformed plant cell In an embodiment of the present disclosure, there is provided a method of generating a transgenic plant as described herein, wherein transformation of said plant cell is carried out by a method selected from the group consisting of *Agrobacterium* mediated transformation method, particle gun bombardment method, in planta transformation method, liposome mediated transformation method, protoplast transformation method, microinjection, and macroinjection.

In a preferred embodiment of the present disclosure, there is provided a method of generating a transgenic plant as described herein, wherein transformation of said plant cell is carried out by *Agrobacterium* mediated transformation method.

In an embodiment of the present disclosure, transient expression of GUS by a promoter having polynucleotide sequence as set forth in SEQ ID NO: 1 is limited to anthers of *eucalyptus* plant.

In an embodiment of the present disclosure, transient expression of GUS by a promoter having polynucleotide sequence as set forth in SEQ ID NO: 4 is limited to anthers of *eucalyptus* plant.

In an embodiment of the present disclosure, transient expression of GUS by a promoter having polynucleotide sequence as set forth in SEQ ID NO: 7 is limited to anthers of *eucalyptus* plant.

Sequences:

```
SEQ ID NO: 1 depicts the full length promoter
sequence
GGAGAGAGTTGATGTGAAGGAATGAGTGTAATACTATAAGAAACAGTTGA

ATCAATAAGTTATTTTTTCATATACAAACACTGAGGACATGATTATTTAA

GCTTTTGTAATACATGAATTCTAAATTGCAAAATAAATGCATGATAGCTT

TAAAAAAAAATTAAAAACAAAATTAAACTTCACTAGTTACAGTTTTTGTT

ACTTTGTGATTCTTATCCAATATTAAATAGAAACCTATATAAAAAATAAT
```

-continued

TTCAATTGGTGTGGGGTGACCATTGTGACACATTCCATACAGGAAATCAT

CCCTCAAGCATATTTTTTATTATTTTTTTTCATAGGAACACTAATGTTAA

ATATTAAGTGAAGAATTAAGCTTTTTAATCTGATATATTTGAACGGTTGA

TTGAAGCTAATGTAAAGGGAAGTGAAAAAGGGATGGAGCTTCCCAATGAC

GTGGCCCAACCGCAAATCGTTATCTCATCCGGCTTCTTCGTTTTCTTTCT

TTTCTAAATCCAGATCTTCAGGCCAATTTGCTTAGAAACAATGCACACCG

GAGAAGCTACCATGCCGTCCTACTTTTATGGATGGCATTGGACGCATACG

GGGCACTTTGCATGCACGGCATGCAGAGAGCAGCCGAAAATGTCTCCGAT

CCTCTCGAGCAAAAACTCGTCAACCATCCGGAAATGTTCACGGGAAGTTT

ATCCATTTCCTATTTCCCAGTCCTTCCCGGATTTAGAACGTTGGCAGCTT

TTCTTGGAAACCAAAAGCGCACATATAAATCGCCTTGCGCAAGTGTGAGG

CTCAGGGAATGGGAAGACGGAGTTCTTAGTCATTGAAAAA

ACCCCGAATCGACGGTTTCAAATCAAGCAGCTGACGGGATCAAGCAGCA

CTGTTTCGCTCTCTTTCGTCCTTCGTCCTCAAGAACATGCGAAAATGGTG

GACACCGAGACCGCCAGAACGATTGTAGGCATTGTC

SEQ ID NO: 2 depicts the forward primer sequence
TGATTACGCCAAGCTTGGAGAGAGTTGATGTGAAG SEQ ID NO: 3 depicts the reverse primer sequence
CCGGGGATCCTCTAGAGACAATGCCTACAATCGTTC SEQ ID NO: 4 depicts the partial promoter sequence
ACCGCAAATCGTTATCTCATCCGGCTTCTTCGTTTTCTTTCTTTTCTAAA

TCCAGATCTTCAGGCCAATTTGCTTAGAAACAATGCACACCGGAGAAGCT

ACCATGCCGTCCTACTTTTATGGATGGCATTGGACGCATACGGGCACTT

TGCATGCACGGCATGCAGAGAGCAGCCGAAAATGTCTCCGATCCTCTCGA

GCAAAAACTCGTCAACCATCCGGAAATGTTCACGGGAAGTTTATCCATTT

CCTATTTCCCAGTCCTTCCCGGATTTAGAACGTTGGCAGCTTTTCTTGGA

AACCAAAAGCGCACATATAAATCGCCTTGCGCAAGTGTGAGGCTCAGGGA

ATGGGAAGACGGAGTTCTTAGTCATTGAAAAAACCCCGAATCGACGGTTT

CAAATCAAGCAGCTGACGGGATCAAGCAGCACTGTTTCGCTCTCTTTCG

TCCTTCGTCCTCAAGAACATGCGAAAATGGTGGACACCGAGACCGCCAGA

ACGATTGTAGGCATTGTC

SEQ ID NO: 5 depicts the reverse primer sequence
ATGATTACGCCAAGCTTACCGCAAATCGTTATCTCAT SEQ ID NO: 6 depicts the reverse primer sequence
ATGATTACGCCAAGCTTGATTTAGAACGTTGGCAGCT SEQ ID NO: 7 depicts the partial promoter sequence
GATTTAGAACGTTGGCAGCTTTTCTTGGAAACCAAAAGCGCACATATAAA

TCGCCTTGCGCAAGTGTGAGGCTCAGGGAATGGGAAGACGGAGTTCTTAG

TCATTGAAAAAACCCCGAATCGACGGTTTCAAATCAAGCAGCTGACGGGG

ATCAAGCAGCACTGTTTCGCTCTCTTTCGTCCTTCGTCCTCAAGAACATG

CGAAAATGGTGGACACCGAGACCGCCAGAACGATTGTAGGCATTGTC

SEQ ID NO: 8 depicts forward primer sequence for
detection of full length or minimal promoter
integration in tobacco
GGAGAGAGTTGATGTGAAG SEQ ID NO: 9 depicts reverse primer sequence for
detection of full length or minimal promoter
integration in tobacco
TGTCTCGGTGTCCACCAT Although the subject matter has been described in considerable detail with reference to certain preferred embodiments thereof, other embodiments are possible. As such, the spirit and scope of the appended claims should not be limited to the description of the preferred embodiment contained therein.

EXAMPLES

The disclosure will now be illustrated with working examples, which is intended to illustrate the working of disclosure and not intended to take restrictively to imply any limitations on the scope of the present disclosure.

Example 1

Isolation and Cloning of EcSWEETp

The forward primer namely IME 2230F having nucleotide sequence as set forth in SEQ ID NO: 2 and reverse primer namely 2231R having nucleotide sequence as set forth in SEQ ID NO: 3 were designed for the promoter region Eucgr.00360, which is homologous to *Eucalyptus.camaldulensis* (Ec) SWEET gene (EcSWEETp). The primers were used to amplify the promoter region from genomic DNA of *Eucalyptus camaldulensis*.

Figure 1:
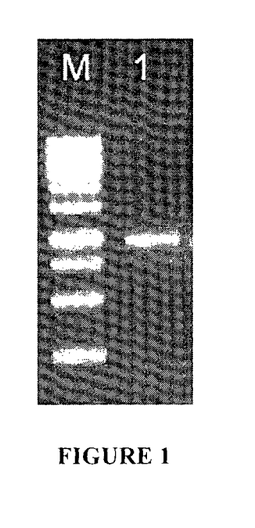
FIG. 1 depicts amplification of EcSWEET promoter region from *Eucalyptus camaldulensis* genomic DNA, in accordance with an embodiment of the present disclosure.
Figure 2:
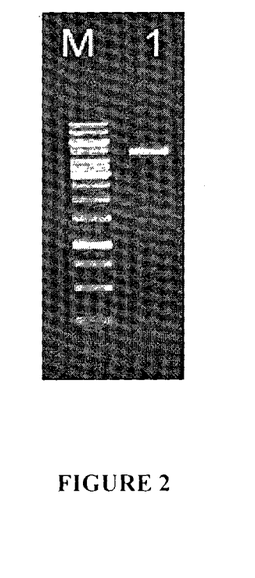
FIG. 2 depicts the plasmid profile of pJET:EcSWEETp, in accordance with an embodiment of the present subject matter.

FIG. 1 shows the amplified polymerase chain reaction (PCR) product (lane designation '1'). Lane designation 'M' represents the molecular DNA ladder. The amplified PCR product thus obtained was cloned in a vector (pJET1.2) and transformed into DH5α *E. coli* cells as shown in FIG. 2 (lane designation 'M' represents the molecular DNA ladder). The recombinant vector is name as pJET:EcSWEETp. Further, the amplified PCR product obtained from the PCR reaction was subjected to sequencing reaction using vector specific primers. The sequencing reaction was carried out using ABI 3730 sequencer at Eurofin sequencing facility in Bangalore. The sequence of the EcSWEETp was analysed online using PLACE (Plant Cis-acting Regulatory DNA Elements) database to find out the signals and possible functions of the promoter region.

Transformation of *E. coli*

The transformation of *E. coli* with different constructs was carried out by heat shock method using (New England Biolabs) NEB *E. coli* DH5α competent cells. Briefly, 10 ng plasmid DNA was mixed with 504 of competent cells and kept on ice for 30 minutes. Heat shock was given at 42° C. for 30 seconds. The mixture was added with 1 mL of SOC medium (2% Tryptone, 0.5% yeast extract, 8.56 mM NaCl, 2.5 mM KCl, 10 mM $MgCl_2$ and 20 mM glucose) and kept at 37° C. for one-hour shaking at 250 RPM. The cells were subsequently plated on LB (10 g tryptone, 5 g yeast extract and 10 g NaCl) plate containing kanamycin (50 μg/mL) as selection antibiotic. Cells were harvested and plasmids were isolated by using Qia prep spin Miniprep kit (Qiagen Cat No. 27104). The sequence of constructs was confirmed by sequencing using vector specific primers with ABI 3730 sequencer at Eurofin sequencing facility at Bangalore.

Example 2

Analysis of EcSWEET Promoter Region by PLACE Software

The sequence of EcSWEET promoter was analysed by online PLACE (Plant Cis-acting Regulatory DNA Elements) to find signals and possible functions in the promoter region. (Table 1)

TABLE 1

List of major elements found in EcSWEETp by PLACE analysis

| No | Factor/Site Name | Signal Sequence | Function |
|---|---|---|---|
| 1 | 2SSEEDPROTBANAPA | (+) CAAACAC | Conserved in storage-protein gene promoters and important for high activity of the napA promoter |
| 2 | ABRELATERD1 | (+) ACGTG | required for etiolation-induced expression of erd1 (early responsive to dehydration) in *Arabidopsis* |
| 3 | ABREOSRAB21 | (+) ACGTSSSC | ABA responsive element (ABRE) of wheat and rice rab21 genes |
| 4 | ACGTATERD1 | (+) ACGT | required for etiolation-induced expression of erd1 (early responsive to dehydration) in *Arabidopsis* |
| 5 | ARFAT | (−) TGTCTC | ARF (auxin response factor) binding site found in the promoters of primary/early auxin response genes of *A. thaliana*. |
| 6 | ARR1AT | (+) NGATT | ARR1-binding element found in *Arabidopsis*; ARR1 is a response regulator |
| 7 | ASF1MOTIFCAMV | (+) TGACG | Involved in transcriptional activation of several genes by auxin and/or salicylic acid |
| 8 | AUXRETGA2GMGH3 | (+) TGACGTGGC | putative auxin-responsive element (AUXRE) E1 of soybean GH3 promoter |
| 9 | BOXIINTPATPB | (+) ATAGAA | Important for the activity of NCII promoter |
| 10 | BOXIIPCCHS | (+) ACGTGGC | Found in the parsley chs genes, Essential for light regulation. |
| 11 | CAATBOX1 | (+) CAAT | CAAT promoter consensus sequence found in legA gene of pea |
| 12 | CANBNNAPA | (+) CNAACAC | Elements found in Embryo- and endosperm-specific transcription of napin (storage protein) gene. |
| 13 | CAREOSREP | (−) CAACTC | CAREs (CAACTC regulatory elements) found in the promoter region of a cystein proteinase (REP-1) gene in rice |
| 14 | CBFHV | (+) RYCGAC | Binding site of barley CBF1, and CBF2; Also known as dehydration-responsive element (DRE) binding proteins (DREBs) |
| 15 | CIACADIANLELHC | (+) CAANNNNATC | Region necessary for circadian expression of tomato Lhc gene |
| 16 | DPBFCOREDCDC3 | (+) ACACNNG | bZIP transcription factors binding core sequence, embryo-specific expression |
| 17 | DRE1COREZMRAB17 | (+) ACCGAGA | DRE1 core found in maize rab17 gene promoter; rab17 is expressed during late embryogenesis |
| 18 | EBOXBNNAPA | (+) CANNTG | E-box of napA storage-protein gene of *Brassica napus* |
| 19 | GATABOX | (+) GATA | Required for high level, light regulated, and tissue specific expression |
| 20 | GT1GMSCAM4 | (+) GAAAAA | Plays a role in pathogen- and salt-induced SCaM-4 gene expression |
| 21 | GTGANTG10 | (+) GTGA | GTGA motif found in the promoter of the tobacco late pollen gene g10. |
| 22 | HEXAT | (+) TGACGTGG | Binding site of *Arabidopsis* bZIP protein TGA1 and G box binding factor GBF1. |
| 23 | IBOX | (−) GATAAG | Conserved sequence upstream of light-regulated genes. |
| 24 | L1BOXATPDF1 | (+) TAAATGYA | L1 box found in promoter of *A. thaliana* PROTODERMAL FACTOR1 (PDF1) gene, Involved in L1 layer-specific expression |
| 25 | LECPLEACS2 | (+) TAAAATAT | Core element in LeCp (tomato Cys protease) binding cis-element in LeAcs2 gene |
| 26 | LTRE1HVBLT49 | (+) CCGAAA | LTRE-1(low-temperature-responsive element) in barley blt4.9 gene promoter. |
| 27 | MARTBOX | (+) TTWTWTTWTT | found in SAR (scaffold attachment region) or matrix attachment region, (MAR). |
| 28 | MYB1AT | (+) WAACCA | MYB recognition site found in the promoters of the dehydration-responsive gene rd22 and many other genes in *Arabidopsis* |
| 29 | MYBCORE | (+) CNGTTR | Binding site for a ATMYB2 involved in regulation of genes that are responsive to water stress in *Arabidopsis* |
| 30 | MYBCOREATCYCB1 | (+) AACGG | found in the promoter of *Arabidopsis thaliana* cyclin B1: 1 gene |

TABLE 1-continued

List of major elements found in EcSWEETp by PLACE analysis

| No | Factor/Site Name | Signal Sequence | Function |
|----|------------------|-----------------|----------|
| 31 | MYBGAHV | (+) TAACAAA | Central element of gibberellin (GA) response complex (GARC) in high-pI alpha-amylase gene in barley |
| 32 | MYCCONSENSUSAT | (+) CANNTG | MYC recognition site found in the promoters of the dehydration-responsive gene rd22 |
| 33 | OSE2ROOTNODULE | (+) CTCTT | One of the consensus sequence motifs of organ-specific elements of the promoters activated in infected cells of root nodules |
| 34 | POLLEN1LELAT52 | (+) AGAAA | One of two co-dependent regulatory elements responsible for pollen specific activation of tomato lat52 gene |
| 35 | PREATPRODH | (−) ACTCAT | Necessary for the efficient expression of ProDH in response to hypoosmolarity |
| 36 | PROLAMINBOXOSGLUB1 | (−) TGCAAAG | Involved in quantitative regulation of the GluB-1 gene |
| 37 | PYRIMIDINEBOXOSRAMY1A | (−) CCTTTT | pyrimidine box is partially involved in sugar repression |
| 38 | RYREPEATBNNAPA | (+) CATGCA | Required for seed specific expression |
| 39 | RYREPEATLEGUMINBOX | (+) CATGCAY | legumin box found in seed-storage protein genes in legumes |
| 40 | SEBFCONSSTPR10A | (−) YTGTCWC | Binding site of the potato silencing element binding factor (SEBF) gene found in promoter of pathogenesis-related gene |
| 41 | SREATMSD | (+) TTATCC | sugar-repressive element (SRE); found in down-regulated genes after main stem decapitation in Arabidopsis |
| 42 | SURECOREATSULTR11 | (+) GAGAC | SURE contains auxin response factor (ARF) binding sequence. |
| 43 | TAAAGSTKST1 | (+) TAAAG | TAAAG motif found in promoter of KST1 gene encoding for a K+ influx channel of guard cells |
| 44 | TATABOX5 | (+) TTATTT | TATA box found in the 5'upstream region of pea glutamine synthetase gene |
| 45 | TATCCAOSAMY | (+) TATCCA | Mediate sugar and hormone regulation of alpha-amylase gene expression. |
| 46 | TATCCAYMOTIFOSRAMY3D | (+) TATCCAY | Responsible for sugar repression. |
| 47 | TGACGTVMAMY | (+) TGACGT | Required for high level expression of alpha-Amylase in the cotyledons of the germinated seeds |
| 48 | WBOXATNPR1 | (−) TTGAC | Recognized specifically by salicylic acid-induced WRKY DNA binding proteins |
| 49 | WBOXNTERF3 | (+) TGACY | Involved in activation of ERF3 gene by wounding. |

Example 3

Cloning and Preparation of Vectors for Minimal Promoter Analysis

Figure 3:
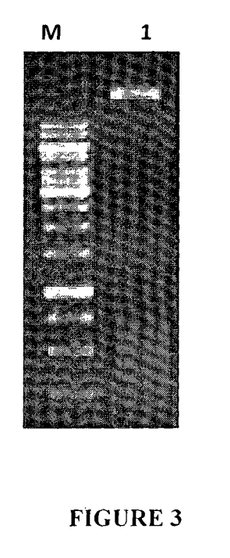
FIG. 3 depicts the plasmid profile of pBI121:EcSWEETp, in accordance with an embodiment of the present subject matter.

Amplification of a nucleotide fragment having size of 976 bp, 518 bp or 247 bp was carried out using forward and reverse primers as set forth in SEQ ID NO: 2 and SEQ ID NO: 3, SEQ ID NO: 5 and SEQ ID NO: 3 and SEQ ID NO: 6 and SEQ ID NO: 3 respectively. The above mentioned three polynucleotide fragments were amplified from the vector pJET:EcSWEETp. The primers carrying engineered XbaI and HindIII recognition sequences were used for the amplication of the three nucleotide fragments. The reactions were carried out in a total volume of 204, with one microgram of plasmid DNA along with 1 unit each of XbaI and HindIII. The promoter region was amplified from pJET:EcSWEETp using forward and reverse primers. As shown in FIG. 3, the PCR product was cloned in to pBI121 vector using infusion cloning reagents as per the manufactures instructions (Takara). The PCR products were ligated in to pBI121 vector and transformed in to NEB5α competent cells. The transformed competent cells were subsequently plated on LB plate with kanamycin (50 µg/mL) as the selection antibiotic. The positive colonies were picked up and were subjected to colony PCR with promoter specific primers. The recombinant nucleic acid constructs namely pBI121:EcSWEETp_976, pBI121:EcSWEETp_518 and pBI121:EcSWEETp_247 having a nucleotide sequence as set forth in SEQ ID NO: 1, SEQ ID NO: 4, and SEQ ID NO: 7 respectively were mobilized into Agrobacterium LBA4404 cells.

Figure 4:
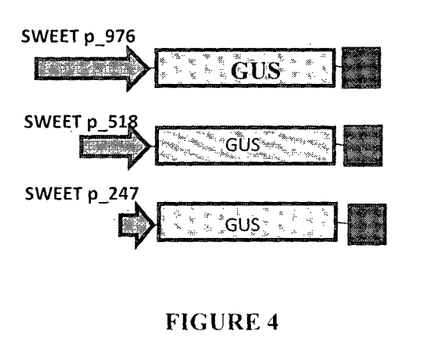
FIG. 4 depicts the deletion constructs used for minimal promoter analysis, in accordance with an embodiment of the present subject matter.

FIG. 4 denotes the graphical representation of the recombinant nucleic acid constructs mobilized in to Agrobacterium LBA4404

Example 4

Transformation of Agrobacterium tumefaciens

All the three promoters constructs as described above were mobilized into Agrobacterium tumefaciens by electroporation with Electromax Agrobacterium LBA4404 cells with the manufactures instructions (Invitrogen). After two days, positive colonies were picked up and were confirmed by inoculating into YM broth (yeast extract 0.04%, Mannitol 1.0%, NaCl 1.7 mM, MgSO$_4$.7H$_2$O 0.8 mM and K$_2$HPO$_4$.3H$_2$O 2.2 mM with streptomycin (100 µg/mL) and kanamycin (50 µg/mL). Cultures were stored in –80° C. in 25% glycerol.

Example 5

Expression Analysis of EcSWEET Gene

Figure 5:
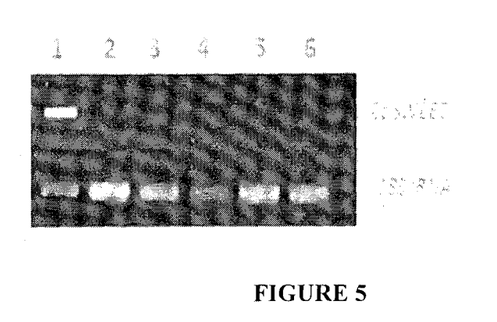
FIG. 5 depicts the expression pattern of the EcSWEET gene transcript in various tissues of *Eucalyptus camaldulensis*, in accordance with an embodiment of the present subject matter.

The transcripts of EcSWEET gene were analyzed in various tissues of *eucalyptus* such as flower, mature leaf, young leaf, xylem, stem and root. FIG. 5 depicts the PCR product obtained indicative for presence or absence of EcSWEET gene transcript. Lane 1 represents EcSWEET transcript signal derived from flower cDNA. Lane 2 represents EcSWEET transcript signal derived from mature leaf cDNA. Lane 3 represents EcSWEET transcript signal derived from young leaf cDNA. Lane 4 represents EcSWEET transcript signal derived from xylem cDNA. Lane 5 represents EcSWEET transcript signal derived from stem cDNA. Lane 6 represents EcSWEET transcript signal derived from root cDNA.

Figure 6:
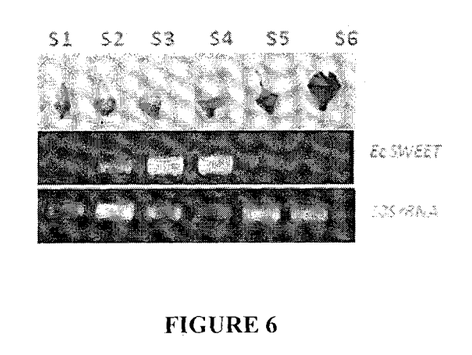
FIG. 6 depicts the stage specific expression pattern of the EcSWEET gene transcript from *Eucalyptus camaldulensis* flowers, in accordance with an embodiment of the present subject matter.

It can be inferred from transcript analysis presented in FIG. 5 that there is no expression for EcSWEET gene in various tissues except in flower. Further analysis as shown in FIG. 6 indicates that the flower specific EcSWEET transcript is expressed preferentially in different stages of flower development. Different stages of flower development were termed as S1, S2, S3, S4, S5, and S6. The transcript analysis in various tissues of S1 through S6 stages revealed that EcSWEET transcript started accumulating from S2 onwards and reached maximum at S4 followed by a drop in the expression in subsequent stages.

Example 6

Male Tissue Specific Promoter Activity of EcSWEETp

Figure 7:
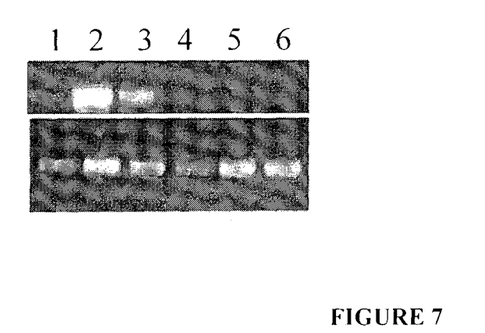
FIG. 7 depicts the stage specific expression pattern of EcSWEET gene transcript from *Eucalyptus camaldulensis* male (androecium) or female (gynoecium) flower parts, in accordance with an embodiment of the present subject matter.

Buds from S2, S3 and S4 stages were further analysed to check whether EcSWEET transcripts showed any specific expression pattern in male or female reproductive organs. Androecium and gynoecium were separated from S2, S3, and S4 bud stages of *Eucalyptus camaldulensis* and transcript analysis of EcSWEET was carried out. FIG. 7 shows that the EcSWEET transcript is specific to male reproductive tissues, which includes filaments and anthers. Lane 1 represents EcSWEET transcript signal in androecium from young bud. Lane 2 represents EcSWEET transcript signal in androecium from mature bud. Lane 3 represents EcSWEET transcript signal in androecium from opened flower. Lane 4 represents EcSWEET transcript signal in gynoecium from young bud. Lane 5 represents EcSWEET transcript signal in gynoecium from mature bud. Lane 6 represents EcSWEET transcript signal in gynoecium from opened flower.

Example 7

Transient Expression of Promoter Constructs in *Eucalyptus*

*Agrobacterium* strain LBA4404 harboring individual constructs (promoter driving expression of GUS) were inoculated in LB broth with kanamycin (50 µg/ml) and streptomycin (100 µg/ml). An overnight culture of *Agrobacterium* (OD600 of 1) was centrifuged at 6000 rpm for 10 minutes and resuspended in 25 ml of infiltration medium (0.5×MS medium, 5 mM MES-KOH (pH 5.6), 200 µM acetosyringone). The bacterial solution was incubated at room temperature for up to three hours with gentle shaking under dark conditions. The tissues were collected from open field and were surface sterilized with Tween 20 (1%) followed by HgCl$_2$ (0.1%). Subsequently, tissues were soaked in *Agrobacterium* solution containing silwet L77 and infiltration was performed by applying vacuum three times with three minute interval. The samples were subsequently put of paper towels to remove excess infiltration medium and placed on 0.5×MS medium (pH 5.6) with 0.6% agar and 50 µg/ml cefotaxime. The samples were returned to grow under initial growing conditions for three days before imaging (Takata et al., Plant Methods, 2012, 8, 30).

Histochemical staining: tissues were transferred to fixing solution (10 mM MES (pH 5.6), with 300 mM mannitol and 0.3% formaldehyde) for 45 minutes at room temperature. After three washes with distilled water, tissues were transferred to staining solution (500 mM sodium phosphate buffer, 0.1 mM potassium ferrocyanide, 0.1 mM potassium ferricyanide and X-glcA (1 mg/ml)). The samples were incubated at 37° C. for up to 24 hours until a blue stain developed. The tissue clearing was performed with 70% ethanol for 1-3 hours (Yu et al., Plant Physiology, 2005, 139, 1853-1869).

Table 2 below lists the differential tissue expression pattern of the three different promoter constructs (FIG. 4).

| Construct   | Gynoecium | Androecium | Leaves |
|-------------|-----------|------------|--------|
| pBl121_976  | –         | +          | –      |
| pBl121_518  | –         | +          | –      |
| pBl121_247  | –         | +          | –      |
| pBl121      | +         | +          | +      |

As seen in Table 2, positive control staining (vector alone) shows blue staining in both male and female reproductive organs and leaves.

The full length promoter (976 bp) as set forth in SEQ ID NO: 1, and both the truncated versions (518 bp) (SEQ ID NO: 4), and (247 bp) (SEQ ID NO: 7) show expression of GUS preferentially in male reproductive parts solely.

Figure 8:
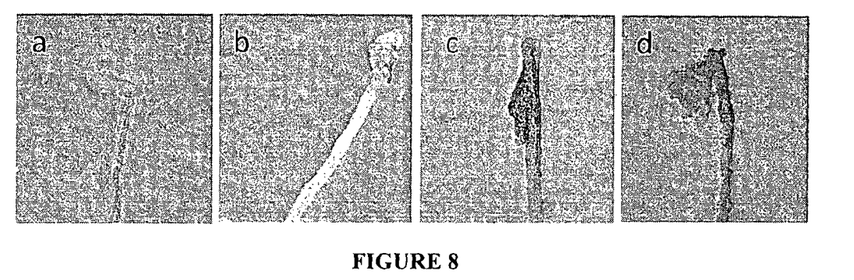
FIG. 8 depicts the results of transient GUS expression pattern in anthers of *eucalyptus* by various promoter constructs, in accordance with an embodiment of the present subject matter.

FIG. 8 depicts the histochemical staining for GUS in anthers of *eucalyptus* infiltrated with various constructs as listed above in Table 2. The full length promoter shows maximal staining intensity (panel d). The minimal promoter shows faint staining (panel b), while the 518 bp (SEQ ID NO: 4) deletion promoter shows intermediate staining intensity in anthers (panel c) (panel a is negative control).

These data overall show that the promoter as described herein, drives expression of an operably linked gene of interest in a tissue specific manner. Additionally, the activity of the promoter is stage specific, and not constitutive.

Example 8

Tobacco Transformation with Promoter Constructs

Tobacco transformation with full length promoter construct (970 bp) (SEQ ID NO: 1) or minimal length promoter construct (247 bp) (SEQ ID NO: 7) was carried out as described elsewhere (Horsch et al., Science, 1985, 227, 1229-1231) with minor modifications. Briefly, leaf discs from a month old in-vitro grown tobacco plants were incubated with *agrobacterium* cell suspension at 28° C. with gentle shaking for 30 minutes. After incubation, leaf discs were transferred to MS plates with BAP (2 mg/L) and NAA (0.2 mg/L) and kept at 25° C. for four days without antibiotics. Excess growth of agrobacteria was removed by washing with cefotaxime (250 mg/L) and explants were transferred to MS media with kanamycin (100 mg/L) and cefotaxime (250 mg/L). Full grown shoots were transferred to 0.5×MS edia (100 mg/L) and cefotaxime (250 mg/L) for rooting.

DNA isolation from different transgenic plants was carried out by Gene JET plant genomic DNA purification kit (ThermoScientific). The integration of different promoter fragments was confirmed using specific primers as set forth in SEQ ID NO: 8 and SEQ ID NO: 9.

Figure 9:
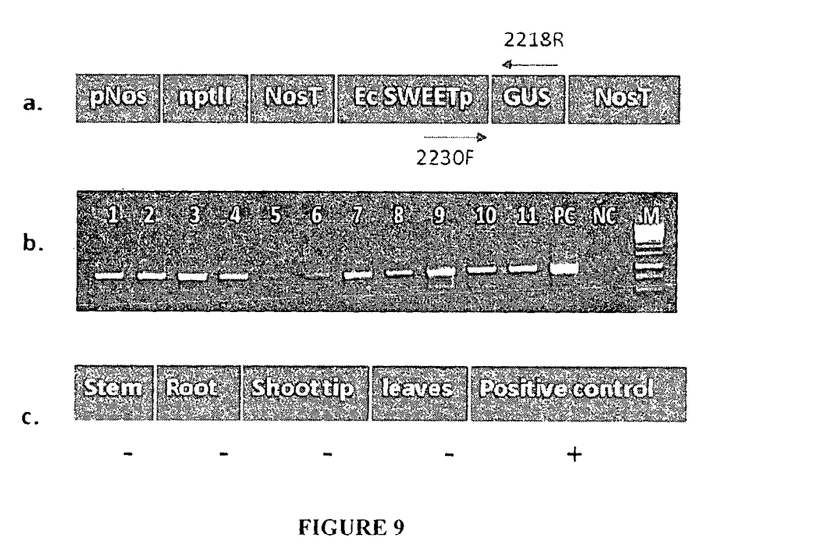
FIG. 9 depicts the activity of full length promoter in transgenic tobacco, in accordance with an embodiment of the present subject matter.

11 transgenic tobacco plants harboring SWEET_970 promoter were evaluated for functional validation. Multiple tissues such as leaf, stem, root, and shoot tips were collected and fixed in formaldehyde solution. As seen in FIG. 9b, confirmation of EcSWEET promoter integration in multiple tobacco plants was done PCR. Histochemical analysis showed that full length promoter activity is absent in stem, root, shoot tip, and leaves (FIG. 9c). FIG. 9a represents the schematic of the elements of the recombinant DNA construct.

Figure 10:
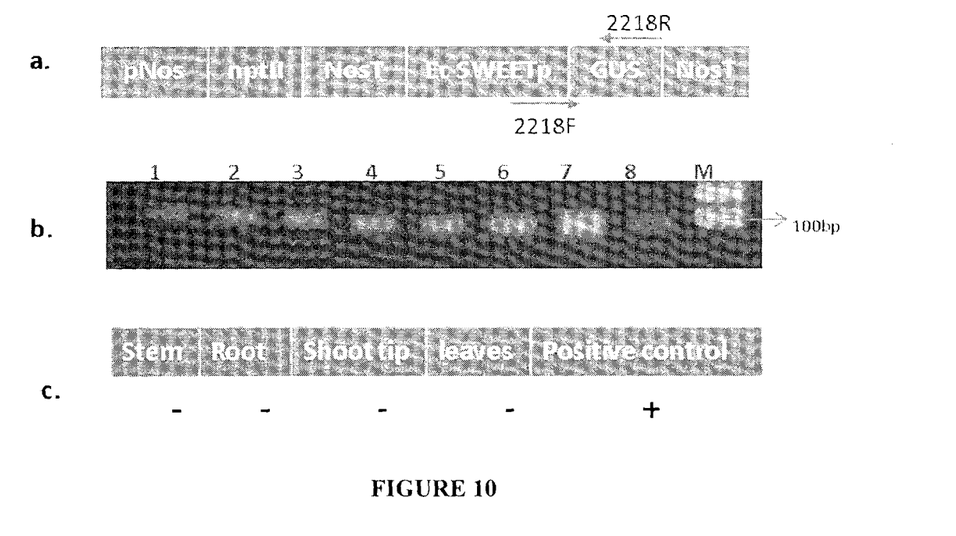
FIG. 10 depicts the activity of the minimal length promoter in transgenic tobacco, in accordance with an embodiment of the present subject matter.

Similarly, 8 transgenic tobacco plants were identified harboring SWEET_247 (FIG. 10b). Similar to FIG. 9c, no GUS staining was observed in any of the tissues tested (FIG. 10c). FIG. 10a represents the schematic of the elements of the recombinant DNA construct.

Overall, these data suggest that the promoter fragment derived from *eucalyptus*, having polynucleotide sequence as set forth in SEQ ID NO: 1 or SEQ ID NO: 4 or SEQ ID NO: 7 is functional and can drive expression in tobacco in a tissue specific manner. In totality, the present disclosure relates to a tissue and sex specific promoter fragment that is active in multiple plant species, and can be used to drive expression of various genes of interest in a temporally and spatially regulated matter.

We claim:

1. A DNA construct comprising a male reproductive tissue-specific promoter operably linked to a heterologous, transcribable polynucleotide, wherein the promoter comprises the nucleotide sequence of SEQ ID NO: 7.

2. The DNA construct of claim 1, wherein the promoter comprises the nucleotide sequence of SEQ ID NO: 4.

3. The DNA construct of claim 1, wherein the promoter comprises the nucleotide sequence of SEQ ID NO: 1.

4. A DNA vector comprising the DNA construct of claim 1.

5. A host cell comprising the DNA construct of claim 1.

6. A host cell comprising the DNA vector of claim 4.

7. The host cell of claim 6, wherein said host cell is a bacterial cell.

8. The host cell of claim 6, wherein said host cell is a plant cell.

9. A transgenic plant or part thereof transformed with the DNA construct of claim 1.

10. The transgenic plant part of claim 9, wherein said part is a seed of the transgenic plant.

11. The transgenic plant or part thereof of claim 9, wherein said transgenic plant is a monocot.

12. The transgenic plant or part thereof of claim 9, wherein said transgenic plant is a dicot.

13. The transgenic plant or part thereof of claim 9, wherein said transgenic plant is selected from the group consisting of: wheat, rice, barley, oats, potato, soybean, tobacco, *eucalyptus*, subabul, *casuarina*, corymbia, poplar, and acacia.

14. A method for generating a transgenic plant capable of driving expression of a desired transcribable, heterologous polynucleotide specifically in male reproductive tissues of the plant, the method comprising the steps of:
   a) obtaining a plant cell;
   b) transforming the plant cell with the DNA construct of claim 1;
   c) growing the transformed plant cells into plant shoots.

15. A method for driving expression of a desired transcribable, heterologous polynucleotide exclusively in male reproductive tissues of a plant, the method comprising the steps of:
   d) transforming plant cells with the DNA construct of claim 2;
   e) producing a transgenic plant from the transformed plant cells;
       wherein the produced transgenic plant expresses the transcribable, heterologous polynucleotide specifically in male reproductive tissues of the transgenic plant.

16. A method for driving expression of a desired transcribable, heterologous polynucleotide exclusively in male reproductive tissues of a plant, the method comprising the steps of:
   f) transforming plant cells with the DNA construct of claim 3;
   g) producing a transgenic plant from the transformed plant cells;
       wherein the produced transgenic plant expresses the transcribable, heterologous polynucleotide specifically in male reproductive tissues of the transgenic plant.

17. The method of claim 14, wherein the transgenic plant is selected from the group consisting of: wheat, rice, barley, oats, potato, soybean, tobacco, *eucalyptus*, subabul, *casuarina*, corymbia, poplar, and acacia.

18. A transgenic plant produced by the method of claim 15.

19. The transgenic plant of claim 9, wherein the expression of the heterologous polynucleotide confers male sterility or pollen ablation to the plant.

20. The transgenic plant of claim 9, wherein the expression of the heterologous polynucleotide confers plant resistant to one or more of: abiotic stress, insecticides, and herbicides.

21. The transgenic plant of claim 9, wherein the expression of the heterologous polynucleotide confers gene excision activity to the plant.

22. A transgenic plant expressing a promoter operably linked to a heterologous, transcribable polynucleotide, wherein the promoter comprises the nucleotide sequence of SEQ ID NO: 7, and wherein the heterologous polynucleotide is expressed in the anthers and filaments of the transgenic plant.

23. The transgenic plant of claim 22, wherein said heterologous polynucleotide is expressed during developmental stages S1, S2, or S3 of the plant.

\* \* \* \* \*

SEQUENCE LISTING

```
<160> NUMBER OF SEQ ID NOS: 9

<210> SEQ ID NO 1
<211> LENGTH: 976
<212> TYPE: DNA
<213> ORGANISM: ARTIFICIAL SEQUENCE
<220> FEATURE:
<223> OTHER INFORMATION: SYNTHETIC SEQUENCE

<400> SEQUENCE: 1
ggagagagtt gatgtgaagg aatgagtgta atactataag aaacagttga atcaataagt      60 tatttttca tatacaaaca ctgaggacat gattatttaa gcttttgtaa tacatgaatt     120
ctaaattgca aaataaatgc atgatagctt taaaaaaaaa ttaaaaacaa aattaaactt     180
cactagttac agtttttgtt actttgtgat tcttatccaa tattaaatag aaacctatat     240
aaaaaataat ttcaattggt gtggggtgac cattgtgaca cattccatac aggaaatcat     300
ccctcaagca tatttttat tattttttt cataggaaca ctaatgttaa atattaagtg     360
aagaattaag cttttaatc tgatatattt gaacggttga ttgaagctaa tgtaaaggga     420
agtgaaaaag ggatggagct tcccaatgac gtggcccaac cgcaaatcgt tatctcatcc     480
ggcttcttcg ttttctttct tttctaaatc cagatcttca ggccaatttg cttagaaaca     540
atgcacaccg gagaagctac catgccgtcc tactttatg gatggcattg gacgcatacg     600
gggcactttg catgcacggc atgcagagag cagccgaaaa tgtctccgat cctctcgagc     660
aaaaactcgt caaccatccg gaaatgttca cgggaagttt atccatttcc tatttcccag     720
tccttcccgg atttagaacg ttggcagctt ttcttggaaa ccaaaagcgc acatataaat     780
cgccttgcgc aagtgtgagg ctcagggaat gggaagacgg agttcttagt cattgaaaaa     840
accccgaatc gacggtttca aatcaagcag ctgacgggga tcaagcagca ctgtttcgct     900
ctctttcgtc cttcgtcctc aagaacatgc gaaaatggtg gacaccgaga ccgccagaac     960
gattgtaggc attgtc                                                   976

<210> SEQ ID NO 2
<211> LENGTH: 35
<212> TYPE: DNA
<213> ORGANISM: ARTIFICIAL SEQUENCE
<220> FEATURE:
<223> OTHER INFORMATION: SYNTHETIC SEQUENCE

<400> SEQUENCE: 2
tgattacgcc aagcttggag agagttgatg tgaag                                35
```

<210> SEQ ID NO 3
<211> LENGTH: 36
<212> TYPE: DNA
<213> ORGANISM: ARTIFICIAL SEQUENCE
<220> FEATURE:
<223> OTHER INFORMATION: SYNTHETIC SEQUENCE

<400> SEQUENCE: 3
ccggggatcc tctagagaca atgcctacaa tcgttc                        36

<210> SEQ ID NO 4
<211> LENGTH: 518
<212> TYPE: DNA
<213> ORGANISM: ARTIFICIAL SEQUENCE
<220> FEATURE:
<223> OTHER INFORMATION: SYNTHETIC SEQUENCE

<400> SEQUENCE: 4
accgcaaatc gttatctcat ccggcttctt cgttttcttt cttttctaaa tccagatctt    60
caggccaatt tgcttagaaa caatgcacac cggagaagct accatgccgt cctactttta   120
tggatggcat tggacgcata cggggcactt tgcatgcacg gcatgcagag agcagccgaa   180
aatgtctccg atcctctcga gcaaaaactc gtcaaccatc cggaaatgtt cacgggaagt   240
ttatccattt cctatttccc agtccttccc ggatttagaa cgttggcagc ttttcttgga   300
aaccaaaagc gcacatataa atcgccttgc gcaagtgtga ggctcaggga atgggaagac   360
ggagttctta gtcattgaaa aaccccgaat cgacggtttt caaatcaagc agctgacggg   420
gatcaagcag cactgtttcg ctctctttcg tccttcgtcc tcaagaacat gcgaaaatgg   480
tggacaccga gaccgccaga acgattgtag gcattgtc                          518

<210> SEQ ID NO 5
<211> LENGTH: 37
<212> TYPE: DNA
<213> ORGANISM: ARTIFICIAL SEQUENCE
<220> FEATURE:
<223> OTHER INFORMATION: SYNTHETIC SEQUENCE

<400> SEQUENCE: 5
atgattacgc caagcttacc gcaaatcgtt atctcat                       37

<210> SEQ ID NO 6
<211> LENGTH: 37
<212> TYPE: DNA
<213> ORGANISM: ARTIFICIAL SEQUENCE
<220> FEATURE:
<223> OTHER INFORMATION: SYNTHETIC SEQUENCE

<400> SEQUENCE: 6
atgattacgc caagcttgat ttagaacgtt ggcagct                       37

<210> SEQ ID NO 7
<211> LENGTH: 247
<212> TYPE: DNA
<213> ORGANISM: ARTIFICIAL SEQUENCE
<220> FEATURE:
<223> OTHER INFORMATION: SYNTHETIC SEQUENCE

<400> SEQUENCE: 7
gatttagaac gttggcagct tttcttggaa accaaaagcg cacatataaa tcgccttgcg    60
caagtgtgag gctcagggaa tgggaagacg gagttcttag tcattgaaaa aaccccgaat   120
cgacggtttc aaatcaagca gctgacgggg atcaagcagc actgtttcgc tctctttcgt   180

```
ccttcgtcct caagaacatg cgaaaatggt ggacaccgag accgccagaa cgattgtagg      240
cattgtc                                                                247

<210> SEQ ID NO 8
<211> LENGTH: 19
<212> TYPE: DNA
<213> ORGANISM: artificial sequence
<220> FEATURE:
<223> OTHER INFORMATION: forward primer for detecting promoter insert in
      transgenic tobacco

<400> SEQUENCE: 8
ggagagagtt gatgtgaag                                                   19

<210> SEQ ID NO 9
<211> LENGTH: 18
<212> TYPE: DNA
<213> ORGANISM: artificial sequence
<220> FEATURE:
<223> OTHER INFORMATION: reverse primer sequence for detection of
      promoter insert in transgenic tobacco

<400> SEQUENCE: 9
tgtctcggtg tccaccat                                                    18
```